US00PP33069P3

(12) United States Plant Patent
Cain

(10) Patent No.: US PP33,069 P3
(45) Date of Patent: May 18, 2021

(54) GRAPEVINE PLANT NAMED 'IFG FORTY-FOUR'

(50) Latin Name: ***Vitis* interspecific hybrid**
Varietal Denomination: IFG Forty-four

(71) Applicant: David Cain, Bakersfield, CA (US)

(72) Inventor: David Cain, Bakersfield, CA (US)

(73) Assignee: International Fruit Genetics, LLC, Bakersfield, CA (US)

( * ) Notice: Subject to any disclaimer, the term of this patent is extended or adjusted under 35 U.S.C. 154(b) by 0 days.

(21) Appl. No.: 16/501,852

(22) Filed: Jun. 19, 2019

(65) Prior Publication Data

US 2020/0404822 P1 Dec. 24, 2020

(51) Int. Cl.
*A01H 5/08* (2018.01)
*A01H 6/88* (2018.01)

(52) U.S. Cl.
USPC ..... Plt./205
CPC ..... *A01H 6/88* (2018.05)

(58) Field of Classification Search
USPC ..... Plt./205
CPC ..... A01H 5/08; A01H 5/0812; A01H 5/02; A01H 5/00; A01H 6/88
See application file for complete search history.

(56) References Cited

U.S. PATENT DOCUMENTS

PP30,325 P2 * 4/2019 Cain ..... A01H 5/08 Plt./205

* cited by examiner

*Primary Examiner* — June Hwu

(57) ABSTRACT

This invention is a new and distinct grapevine variety denominated 'IFG Forty-four'. The new grapevine is characterized by producing small naturally seedless reddish black berries having an ellipsoid shape with a Concord like labrusca flavor. Fruits normally ripen early-season, about mid to late July near Delano Calif. Fruits are fairly low in acidity, with a soft to slightly firm texture. Berries color readily even in hot climatic conditions and produce completely colored dark reddish black berries. Vines are very productive and can be pruned to short spurs.

1 Drawing Sheet

Latin name of the genus and species claimed: *Vitis* interspecific hybrid.

Variety denomination: 'IFG Forty-four'.

BACKGROUND OF THE INVENTION

The new and distinct Grapevine plant described and claimed herein originated from a hand pollinated cross of '04044-035-217' (unnamed *Vitis* interspecific hybrid selection from the IFG breeding program) and '07019-069-193' (unnamed *Vitis* interspecific hybrid from the IFG breeding program) hybridized in May 2011. The abortive seed traces were subsequently embryo cultured and the resulting 58 seedlings were planted in the field in April 2012. The present variety of grapevine was selected as a single plant in July 2013 and was first asexually propagated by hardwood cuttings in December 2013 near Delano, Kern County, Calif. These resulting cuttings produced second generation plants that were planted during April 2014 near Delano, Kern County, Calif. and were observed for four years and found to reproduce true-to-type.

BRIEF SUMMARY OF THE INVENTION

The new grapevine 'IFG Forty-four' is characterized by producing small naturally seedless reddish black berries having an ellipsoid shape with a Concord like labrusca flavor. Fruits normally ripen early-season, about mid to late July near Delano Calif. Fruits are fairly low in acidity, with a soft to slightly firm texture. Berries color readily even in hot climatic conditions and produce completely colored dark reddish black berries. Vines are very productive and can be pruned to short spurs. Clusters are medium size, moderately loose, and require sizing with gibberellic acid to enlarge berry size. The new grapevine differs from its maternal parent, '04044-035-217' selection by having dark reddish black rather than white berries, by ripening approximately three weeks earlier, by having a smaller, cluster, berry and seed trace size. 'IFG Forty-four' has a strong Concord flavor rather than a neutral flavor of the '04044-035-217'. 'IFG Forty-four' can be distinguished from its pollen parent, '07019-069-193', by having a ellipsoid rather than round berry shape, by having full black rather than reddish black berry color, by having a concord rather than a citrus-like concord flavor and by having softer flesh texture. 'IFG Forty-four' ripens approximately two weeks earlier than the '07019-069-193'.

'IFG Forty-four' is most similar to 'IFG Thirty-four' (U.S. Plant Pat. No. 30,325). 'IFG Forty-four' differs from 'IFG Thirty-four', by having an ellipsoid rather than round berry shape, by having softer, less tough skin texture, by having a smaller natural berry size, and by having a larger, heavier cluster with more berries per cluster. Leaves of 'IFG Forty-four' are larger and have a U-shaped base of the upper leaf sinus rather than the V-shaped base of the upper leaf sinus of 'IFG Thirty-four'.

BRIEF DESCRIPTION OF THE DRAWING

The accompanying photographic drawing illustrates in full color a 4-year-old plant of 'IFG Forty-four'. The photograph was taken outdoors with indirect lighting. The colors are as nearly true as is reasonably possible in a color representation of this type. The fruit depicted in the drawing is in its natural state and has not been treated with gibberellic acid. The drawing is of a mature leaf, a mature fruit cluster, a typical berry in cross section and a young shoot tip.

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2015 by The Royal Horticultural Society, London, England.

Throughout this specification, subjective description values conform to those set forth by the UPOV International Union for the Protection of New Varieties of Plants publication 'Grapevine *Vitis* L. Guidelines'.

The descriptive matter which follows pertains to 'IFG Forty-four' plants grown in the vicinity of Delano, Kern County, Calif. during 2018 and 2019 and is believed to apply to plants of the variety grown under similar conditions of soil and climate elsewhere:

VINE

General:

*Vigor*.—Vigorous.
*Density of foliage*.—Dense.
*Productivity*.—Productive, producing about 24.9 to 37.3 kg of fruit per vine.
*Root stock*.—Own root.
*Training method*.—Typically spur pruned leaving 2 bud spurs.
*Plant hardiness zone*.—Fully hardy in USDA zone 9A (2012). Not tested in other zones.

Trunk:

*Trunk diameter of* 4-*year-old vines at* 30 *cm above the soil line*.—About 4.4 cm.
*Shape*.—Medium to somewhat stocky.
*Straps*.—Short, split.
*Surface texture*.—Medium rough texture.
*Inner bark color*.—Greyed-orange: 175A.
*Outer bark color*.—Grey: 201A.

SHOOTS

Young shoot:

*Form of tip*.—Wide open.
*Distribution of anthocyanin coloration of tip*.—Overall: Greyed-purple: 187B.
*Intensity of anthocyanin coloration of tip*.—Weak.
*Density of prostrate hairs on tip*.—Medium.
*Density of erect hairs on tip*.—Absent.
*Color*.—Yellow-green: 144A.

Woody shoot (mature canes):

*Internode length*.—Long: About 13.9 cm.
*Width at node*.—About 1.1 cm.
*Cross section*.—Circular.
*Surface*.—Striate.
*Main color*.—The following colors were observed: Greyed-orange: 166C and 166D.
*Density of erect hairs on nodes*.—None or very sparse.
*Density of erect hairs on internodes*.—None or very sparse.
*Axillary shoot length at full bloom*.—Weak to medium: Approximately 9.7 cm.

Flowering shoot:

*Vigor during flowering*.—Medium to strong.
*Attitude during flowering on shoots not tied*.—Semi-drooping.
*Color*.—Dorsal side of internodes — Yellow-green: 144A.
*Color*.—Ventral side of internodes — Yellow-green: 144A.
*Color*.—Dorsal side of nodes — Yellow-green: 144A.
*Color*.—Ventral side of nodes — Yellow-green: 144A.
*Density of prostrate hairs on nodes*.—Medium.
*Density of erect hairs on nodes*.—None.
*Density of prostrate hairs on internode*.—Medium.
*Density of erect hairs on internode*.—None.
*Anthocyanin coloration of buds*.—Absent.

Tendrils:

*Distribution on the shoot* (*at full flowering*).—Discontinuous.
*Length of tendril*.—Medium: About 18.8 cm.
*Thickness of tendril* 2 *cm from base*.—About 2.2 mm.
*Color*.—Yellow-green: 144B.
*Form*.—Bifurcated.
*Number of consecutive tendrils*.—2.

LEAVES

Young leaves:

*Color of upper surface of first four distal unfolded leaves*.—Yellow-green: 144A.
*Color of lower surface of young leaves*.—Yellow-green: 144A.
*Average intensity of anthocyanin coloration of six distal leaves prior to flowering*.—Absent or very weak: Greyed-purple: 187B.
*Density of prostrate hairs between veins* (*lower surface*).—Sparse to medium.
*Density of prostrate hairs on veins* (*lower surface*).—Sparse to medium.
*Density of erect hairs between veins* (*lower surface*).—Absent.
*Density of erect hairs on veins* (*lower surface*).—Absent to very sparse.

Mature leaves (opposite first cluster):

*Average length*.—About 12.1 cm.
*Average width*.—About 15.2 cm.
*Mature leaf size*.—Large.
*Shape of blade*.—Wedge-shaped.
*Number of lobes*.—5.
*Blade venation*.—Palmate.
*Anthocyanin coloration of main veins on upper side of blade*.—Absent to very weak on a few leaves: Greyed-purple: 184A.
*Mature leaf profile*.—Undulate.
*Blistering surface of blade upper surface*.—Very weak.
*Leaf blade tip*.—In the horizontal plane of the leaf mid-vein. Does not appear to curve downward.
*Leaf apex*.—Elongated acute.
*Leaf margin*.—Serrate.
*Undulation of margin*.—Medium.
*Undulation of blade between main and lateral veins*.—Slight.
*Shape of teeth*.—Mixture of both sides straight and both sides convex.
*Length of teeth*.—Medium to long.
*Ratio length/width of teeth*.—Medium.
*Shape of upper lateral sinuses*.—Open.

*Depth of upper lateral sinuses*.—Shallow.
*General shape of petiole sinus*.—Half open.
*Shape of base of upper leaf sinuses*.—U-shaped.
*Tooth at petiole sinus*.—Absent.
*Density of prostrate hairs between veins on lower surface of blade*.—Very sparse.
*Density of erect hairs between veins on lower surface of blade*.—Absent.
*Density of prostrate hairs on main veins on lower surface of blade*.—Sparse.
*Density of erect hairs on main veins on lower surface of blade*.—Sparse.
*Density of prostrate hairs on main veins on upper surface of blade*.—None or very sparse.
*Density of erect hairs on main veins on upper surface of blade*.—None.
*Autumn coloration of leaves*.—Greyed-yellow: 162A.

Upper surface:
*Color*.—Green: 137B.
*Anthocyanin intensity and coloration of main veins* (*upper surface*).—Absent to very weak: Greyed-purple: 184A.
*Color of main veins*.—Yellow-green: 145A.
*Surface appearance*.—Semi-glossy.
*Blistering surface of blade*.—Absent to very weak.

Lower surface:
*Color*.—Yellow-green: 146C.
*Anthocyanin coloration of main veins* (*lower surface*) .—Absent.
*Color of main veins*.—Yellow-green: 145C.
*Glossiness*.—Weak.
*Surface texture*.—Smooth.
*Surface appearance*.—Dull.

Petiole:
*Length*.—About 16.5 cm.
*Diameter of petiole 2 cm from blade*.—About 3.3 mm.
*Petiole color*.—The following colors were observed: Yellow-green: 145A and slight amount of Greyed-purple: 184A near the leaf base.
*Length of petiole compared to middle vein*.—Slightly longer.
*Density of prostrate hairs on petiole*.—None or very sparse.
*Density of erect hairs on petiole*.—None or very sparse.

Buds:
*Bud fruitfulness*.—Basal: mostly fruitful.
*Position of first fruitful shoot on previous season cane*.—$1^{st}$ to $2^{nd}$ node.
*Dormant bud length*.—About 6.5 mm.
*Dormant bud width in the proximal/distal plane*.—About 5.7 mm.
*Dormant bud color*.—The following colors were observed: Greyed-orange: 166A and 166B.
*Time of bud burst*.—Midseason: About Mar. 14, 2018.

FLOWERS

General:
*Flower sex*.—Hermaphrodite.
*Length of single flower, unopened*.—About 3.2 mm.
*Width of single flower*.—Unopened: About 2.0 mm. Opened: About 6.3 mm.
*Stamen length*.—About 3.6 mm.
*Stamen count*.—5.
*Pollen color*.—Yellow: 10B.
*Pistil length*.—About 3.6 mm.
*Pistil color*.—Yellow-green: 144A.
*Length of first inflorescence*.—Long: About 20.8 cm long by 17.3 cm wide.
*Position of first flowering and fruiting node*.—$4^{th}$ to $6^{th}$ node (current season growth).
*Number of inflorescence per flowering shoot*.—Up to 1: About 1.
*Time of bloom*.—Mid-season as compared with similar varieties in the growing area of Delano, Calif.
*Date of full bloom*.—About May 7, 2018.

FRUIT

General:
*Ripening period*.—Early: Approximately Jul. 18, 2018.
*Use*.—Fresh market.
*Keeping quality*.—Average.
*Resistance to*.—Insects: Average typical of *Vitis vinifera* species. Diseases: Average typical of *Vitis vinifera* species.
*Refractometer test*.—Soluble solids: About 19.4 Brix.
*Brix/acid*.—About 29.8.
*Titratable acidity*.—About 0.65.
*Juice ph*.—About 3.7.
*Juice color*.—Greyed-orange: 174B.

Cluster:
*Mature cluster length* (*peduncle excluded*).—About 19.3 cm.
*Mature cluster width*.—About 18.8 cm.
*Mature cluster weight*.—About 829.5 g.
*Bunch density*.—Loose: single berries easily separated from each other, some pedicels visible.
*Number of berries*.—About 218.
*Form*.—Conical.

Peduncle:
*Lignification of peduncle*.—Weak.
*Diameter of peduncle*.—About 5.2 mm.
*Length of peduncle*.—Medium long: Approximately 6.8 cm.
*Color of peduncle*.—Yellow-green: 145A.

Berry:
*Uniformity of size*.—Uniform.
*Single berry weight*.—About 3.8 g natural: to about 5.9 g when treated with gibberellic acid.
*Shape*.—Ellipsoid.
*Seeds*.—Contains small rudimentary seed traces.
*Cross section*.—Circular.
*Berry dimensions*.—Longitudinal axis: About 21.2 mm: Horizontal axis: About 16.3 mm.
*Pedicel length*.—About 11.0 mm.
*Pedicel width*.—About 1.8 mm.
*Pedicel color*.—Yellow-green: 145A.
*Berry firmness*.—Soft.
*Particular flavor*.—Concord.
*Bloom* (*cuticular wax*).—Strong.
*Berry separation from pedicel*.—Medium.
*Skin color* (*without bloom*).—Greyed-purple: N186A.
*Flesh color*.—Green-white: 157B.
*Anthocyanin coloration of flesh*.—Absent.

Skin:
*Thickness*.—Medium.
*Skin toughness*.—Not notable when chewing.
*Reticulation*.—Absent.
*Tenacity*.—Tenacious to flesh.

What is claimed:

1. A new and distinct variety of grapevine as herein illustrated and described.

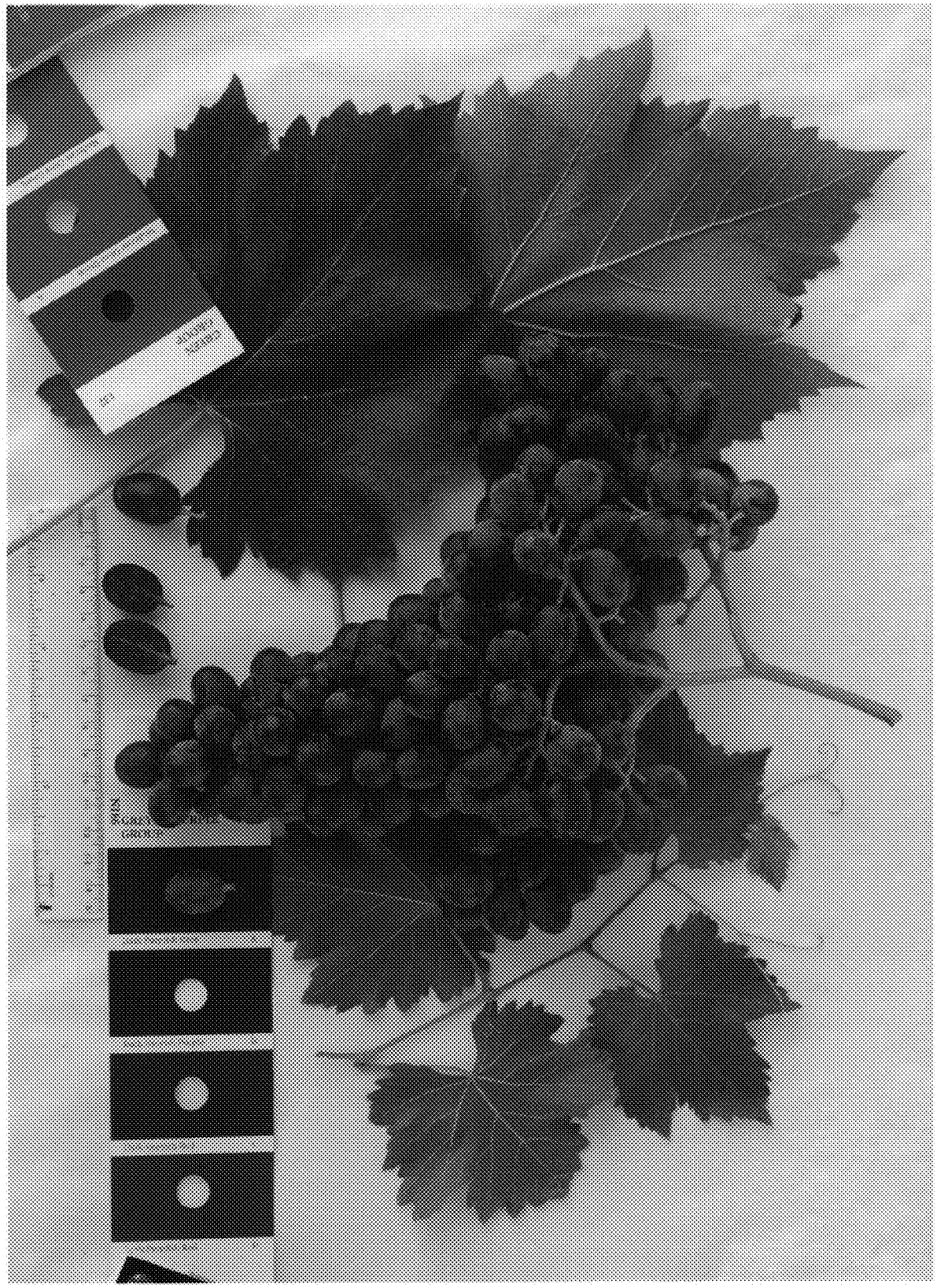

* * * * *